(12) United States Patent
de Haan et al.

(10) Patent No.: US 6,399,594 B2
(45) Date of Patent: *Jun. 4, 2002

(54) STABILIZED TIBOLONE COMPOSITIONS

(75) Inventors: Pieter de Haan, Oss; Theodora Antonia Maria Lambregts v.d. Hurk, Veghel, both of (NL); Ryoichi Morita, Nara (JP); Adrianus Cornelis Petrus Rovers, Son; Jocominus Antonius Maria Zwinkels, Nistelrode, both of (NL)

(73) Assignee: Akzo Nobel NV, Arnhem (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 18 days.

(21) Appl. No.: 09/403,139
(22) PCT Filed: Apr. 20, 1998
(86) PCT No.: PCT/EP98/02361
 § 371 Date: Oct. 14, 1999
(87) PCT Pub. No.: WO98/47517
 PCT Pub. Date: Oct. 29, 1998

(30) Foreign Application Priority Data

Apr. 22, 1997 (EP) .............................................. 97201180

(51) Int. Cl.$^7$ ................................................ A61K 31/56
(52) U.S. Cl. ........................................ 514/177; 424/465
(58) Field of Search ........................... 514/177; 424/465

(56) References Cited

U.S. PATENT DOCUMENTS 4,701,450 A    10/1987  Kelder et al.

FOREIGN PATENT DOCUMENTS

| EP | 0 389 035 A | 9/1990 |
| EP | 0 613 687 A | 9/1994 |
| EP | 0 707 848 A | 4/1996 |
| WO | WO 95 06461 A | 3/1995 |

Primary Examiner—James H. Reamer
(74) Attorney, Agent, or Firm—Mark W. Milstead

(57) ABSTRACT

The invention pertains to a pharmaceutical dosage unit, such as a tablet or a capsule, comprising an effective amount of tibolone (generally of from 0.1 to 10% by weight) and a starch-containing pharmaceutically acceptable carrier (also denoted as basic granulate), wherein the carrier contains of from 10 to 100% by weight of the starch. Thus a more stable tibolone formulation is obtained, allowing dry storage and lower doses of active ingredient.

11 Claims, No Drawings

STABILIZED TIBOLONE COMPOSITIONS

The invention pertains to a pharmaceutical dosage unit, such as a tablet or a capsule, comprising an effective amount of tibolone (generally of from 0.1 to 10% by weight) and a pharmaceutically acceptable carrier, the carrier containing a water-insoluble starch product.

Compositions comprising tibolone, (7α,17α)-17-hydroxy-7-methyl-19-nor-17-pregn-5(10)-en-20-yn-3-one (hereinafter also denoted as "Org OD 14") and a pharmaceutically acceptable solid carrier have been described in EP 389 035, which disclosure is incorporated herein by reference. Tablets are available on the market under the name of Livial®.

Another disclosure in which reference is made to compositions comprising tibolone are EP 707 848 and U.S. Pat. No. 4,701,450. These are not the customary formulations known in practice.

A typical known formulation for tibolone is a 100 mg dosage unit having 2,5 mg of tibolone contained therein, a relatively small amount (e.g. approximately 1% by weight) of pharmaceutically acceptable auxiliaries, and a carrier making up the body of the tablet. The carrier typically is composed of 10% by weight of starch, e.g. potato starch, and 90% by weight of lactose, optionally with other non-starch ingredients such as amylopectin (see, e.g., U.S. Pat. No. 4,701,450) or special types of cellulose, such as microcrystalline celluloses like Avicel (see, e.g., EP 707 848).

The known tablets can be stably stored very well for, typically, 2 years at ambient temperature. A sufficiently humid atmosphere (e.g. 50–70% relative humidity) makes for a better storage stability than a relatively dry atmosphere (e.g. 45% relative humidity or below that). It is an object of the invention to further improve upon the storage stability, in that particularly the shelf-life under relatively dry circumstances is enhanced. Further desirable objectives are that the stability is enhanced in an absolute sense, and also that dosage forms having a lower content of tibolone (which are more prone to stability problems than regular dosage forms) can be suitably kept for a prolonged period.

The invention serves to meet these objectives by providing tibolone dosage units of the above-identified type, wherein the carrier contains more than 10% by weight of the starch product.

Surprisingly, increasing the amount of starch used in the carrier serves as a novel method of making a dosage unit comprising tibolone with an improved stability. It should be noted that a dosage unit comprising tibolone in this invention is intended to mean any dosage unit in which either tibolone substantially alone, or tibolone together with its impurities and/or degradation products, is present as a medicinal agent. The desired stability refers to the situation in which the relative amount of impurities and/or degradation products formed upon storage is as low as possible. The absolute amount of such products will depend, of course, on the amount initially present. E.g., a simple degradation product such as that in which only the double bond is rearranged, might be introduced on purpose at a predetermined level. Important is that this level will remain sufficiently constant during storage, which is the case with the dosage units according to the invention, also in dry circumstances.

The dosage units of the invention not only provide substantively better stability as such, but, moreover, they surprisingly provide the possibility to incorporate a lower amount of tibolone. The customary amount of tibolone in the known dosage unit is 2.5 mg in tablets or capsules of 100 mg, i.e. 2.5%. For the sake of providing therapies better tailored to the individual woman's needs, it is desired to provide dosage units having a lower amount. However, if a known formulation with 10% of starch is adapted by simply including a lower amount of tibolone, the stability of the dosage unit is substantially decreased. E.g., if a 2.5 mg tibolone dosage unit has a shelf-life of, e.g., 2–3 years at room temperature, the same unit upon lowering the amount of tibolone to e.g. 0.3 mg can only be kept at 4° C. for a period of 6–12 months. Such a lower stability being unacceptable in daily practice, it is a great advantage of the present invention that tibolone dosage units can be provided which have a low tibolone content, i.e. 2% by weight or less and, preferably, 1% by weight or less, and yet display sufficient stability. This advantage being manifest particularly if the starch content in the carrier is at least 40% by weight, higher contents are preferred. The content of the starch product more preferably is at least 50% by weight, and most preferably of from 90 to 100% by weight. As particularly upon using lower amounts of tibolone higher polysaccharide contents are preferred, the ratio of the weight percentage of tibolone and the starch percentage in the carrier plays a role in the present invention. Preferably, this ratio is at most 0.02.

The pharmaceutical dosage units of the present invention will generally take the form of tablets or capsules, but other solid or dry pharmaceutical preparations are included. Methods for making such dosage units are well known. For example in the standard English language text Gennaro et al., Remington's Pharmaceutical Sciences, (18th ed., Mack Publishing Company, 1990, see especially Part 8: Pharmaceutical Preparations and Their Manufacture), methods of making tablets, capsules and pills and their respective components are described.

Three methods of making tablets and capsules include the wet-granulation, dry-granulation, and direct compression methods.

Wet-granulation methods involve weighing out ingredients (actives and excipients, including a solvent), mixing the ingredients, granulating them, screening them damp, drying them, dry screening, lubrication, and compressing the resultant admixture into tablets or filling capsules with it. Such procedures result in tablets or capsules having at least adequate homogeneity.

Direct compression methods involve weighing out direct-compression vehicles (including carriers) and active ingredients, mixing of the ingredients, lubrication, and compressing the resulting admixture into tablets, or filling capsules with it.

In the case of steroids, such as tibolone, when making dosage units with only very low doses of the active compound per tablet (e.g. <1.0 milligrams (mg)/100 mg tablet), a problem may occur in that the compound does not always distribute entirely evenly throughout a tableting mixture possibly resulting in some tablets having relatively high amounts of steroid (i.e. "superpotent tablets"), while others have very low amounts of steroid. In this respect a suitable method of making the dosage units that according to the invention are preferred, viz. those having relatively low amounts of tibolone, is a dry-mix procedure such as disclosed in EP-A-0 503 521.

Carriers for active substances in pharmaceutical dosage units generally are in one of two forms. A carrier can be a direct compression carrier, i.e. a material (usually an agglomerate) which does not need to be granulated but can be compressed, after mixing with, e.g., active ingredients, so as to form a dosage unit having material of desired shape, or it can be in the form of a basic granulate. Thus, the carriers of the present invention will be generally in the form of an agglomerate or basic granulate containing the water-insoluble starch product. The tibolone can be directly incorporated into the agglomerates or granulates, using wet-granulation techniques, but most preferably the tibolone is dry-mixed with wet-granulated dry carriers and/or with direct compression carriers.

Wet granulation distinguishes from dry granulation and dry-mixing in that water is applied in wet granulation to produce agglomeration or granules.

The most widely used granulation methods in the pharmaceutical industry are the fluidized bed granulation and the wet-massing method in which a liquid is added to a powder or granulate in a vessel equipped with any type of agitation that will provide granules or agglomerates. Various operations can be recognised in the wet (massing) granulation, including milling of excipients, mixing of milled powders, preparation of binder solution, mixing the binder solution with the powder mixture to form the wet mass, granulation of the mass, coarse screening of wet mass, drying moist granules, and screening dry granules. It is obvious that, depending on the selected excipients and the size of the batch and the selected equipment, some of the operations can be combined or are not required or particular operations can be included. General methods of preparing granules are for instance described in Pharmaceutical Dosage Forms: Tablets (Volume I). Ed. H. A. Lieberman, L. Lachman, J. B. Schwartz (1989), Marcel Dekker Inc. New York and Basel pp. 131–190.

Advantages of wet granulation include improvement of the cohesiveness and compressibility of powders, a good particle size distribution, reduction of a great deal of dust and airborne contamination, prevention of segregation of components.

Small-scale production can be achieved by mixing and wetting the mass in mortars or stainless steel bowls, whereas for larger quantities twin-shell blenders, double-cone blenders, planetary mixers, rotary granulators, high shear mixers and fluid-bed granulation equipment can be applied. General mixing methods are disclosed in Pharmaceutical Dosage Forms (Volume 2). Ed. H. A. Lieberman, L. Lachman, J. B. Schwartz (1990), Marcel Dekker Inc. New York and Basel pp. 1–71. The dry excipients and, optionally, active ingredients are mixed in a suitable mixer, preferably a mixer in which both mixing and granulating can be performed, for instance a Gral high shear mixer, after which an aqueous binder solution is added. Another preferred method is suspending the active ingredients into the aqueous binder solution, which suspension is added to the dry mixture of excipients and granulated.

Granulates, tablets, and capsules prepared by wet-granulation or direct compression consist of several inert materials that can be found in conventional solid oral dosage forms in general The ingredients can be classified in excipients which help to impart satisfactory processing and compression characteristics to the formulation like diluents, stabilising agents, binders, glidants and lubricants and in excipients to give the desirable physical characteristics to the finished tablet like disintegrants and colours. If required the tablets can be provided with a film coat, for instance as disclosed in Pharmaceutical Dosage Forms (Volume 3). Ed. H. A. Lieberman, L. Lachman, J. B. Schwartz (1990), Marcel Dekker Inc. New York and Basel pp. 93–125.

Diluents ("filling excipients") usually make up the major portion of the carrier. Direct compression carriers are described in the same textbook, Volume 1, second edition, Chapter 4, pages 195–246. The direct compression carriers can be classified into groups including water soluble polyalcohols such as lactose (including spray-dried lactose and anhydrous lactose), and polysaccharides such as the group of celluloses (e.g. Avicele® PH 101, PH 102, and PH 200, purified wood cellulose), and the group of water-insoluble starch products according to the invention (e.g. Starch 1500, potato starch, corn starch, wheat starch, including modified starches, agglomerated starches, granulated starches). Corn starch is the most preferred choice.

As mentioned above, according to the present invention the starch products make up more than 10% by weight of the carrier. Since these carrier materials are known for their capacity as disintegrants, i.e. components incorporated into the tablets and capsules to help them break up and dissolve to release the active component, employing them as a building block for dosage units, and therewith attaining the aforementioned stability advantages, is quite contrary to what is known. In addition, of course, other disintegrating agents can be added to the formulation, to the extent needed for having the desired disintegration. Typically such agents, apart from the modified or unmodified starches and celluloses, are clays, cross-linked polyvinylpyrrolidone (PVP), gums, or algins.

Binding agents or adhesives are used as substances that bind powders together and provide cohesiveness to the granulates and tablet formulation. Binders can be added dry and blended with the diluents and, optionally, the drug. In this case binders are activated by addition of water or other solvents. In other manufacturing procedures, the adhesives are dissolved or slurried in a liquid and, in this form, added to the mixed powders. Conventional binders include gelatine, water soluble modified starch, and sugars as sucrose, glucose, dextrose, molasses and lactose. Natural and synthetic gums which have been used include tragacanth, magnesium aluminium silicate, acacia, ammonium calcium alginate, sodium alginate, carboxymethylcellulose, hydroxypropylcellulose, methylcellulose, hydroxypropylmethylcellulose, polyvinylpyrrolidone, polyethylene glycol and clays like Veegum. Depending on for example the solubility of the binders in the various liquids, the binder can be added to the powder mix as a solution in water, or a water-solvent mixture.

In addition to the stabilising effect of the present invention, stabilising agents can be added to further reduce decomposition of tibolone if desired. Examples of such stabilising agents are of the group of antioxidants (such as ascorbyl palmitate and ascorbyl stearate) and the group of water soluble chelating agents (such as sodium EDTA and sodium ascorbate).

Materials to improve the flow characteristics are referred to as glidants. As an example, silicon dioxide, magnesium lauryl sulfate, magnesium aluminium silicate, magnesium oxide, talc or clays can be incorporated into the formulation to reduce interparticulate friction and to eliminate the problems associated with the flow of materials from larger to smaller apertures in the tablet presses.

Before filling capsules or sachets, or compressing tablets, lubricants are mostly added to prevent friction and wear during processing. Some of the lubricants also demonstrate anti-adherent properties that can be relevant in case of sticking of tablet granulations to the faces of the punches and the die walls. Examples of the group of lubricants are the metallic stearates (magnesium stearate), talcum, stearic acid, sodium stearyl fumarate, hydrogenated vegetable oil, and high melting point waxes.

The invention also pertains to a method of making dosage units as described according to the invention. This method involves the steps of providing a carrier of the desired composition (i.e. either as a direct compression carrier or by first making a basic granulate), mixing tibolone, and optionally stabilising agents, with a portion of the eventually needed amount of carrier (e.g. 5–25% by weight, to obtain a pre-mix, screening the pre-mix (e.g. 100–1000 μm, preferably about 250 μm), further mixing it with the remaining portion of the carrier, and finally admixing with lubricant. The process of the invention, apart from being a highly suitable method of making the novel dosage units described hereinbefore, has an additional advantage in those case were fatty acid-derived additional stabilisers are added, such as ascorbyl palmitate. While these substances are hard to process by means of wet granulation, processing them as above, i.e. by admixing them to only a portion of the carrier, makes for an efficient process to obtain a good product.

The invention is further illustrated by the following examples.

EXAMPLE 1

The active ingredient was processed to a homogeneous granulation comprising (per dosage unit):

| | |
|---|---|
| Tibolone (Org GD 14) | 0.3 mg |
| hydroxypropylcellulose | 1.95 mg |
| corn starch | 32.5 mg |
| magnesium stearate | 0.325 mg |
| lactose | to 65 mg |

For a 1 kg batch a Gral 10 high shear mixer was filled with lactose 200 M and corn starch. After mixing for 1 minute a dispersion of Tibolone in an aqueous granulation solution of hydroxypropylcellulose was added quantitatively to the mass. Then 25 ml of water was used to rinse the beaker and subsequently added to the mixture. The mixture was granulated with the Gral 10 for 2.5 minutes. The obtained wetted mass was dried for 4 h in a Marius vacuum cabinet under diminished pressure at 40 degrees Celsius. After drying and screening through a 710 micrometer sieve with an Erweka apparatus the granulate was admixed with magnesium stearate. The granulate was compressed to tablets of 65 mg.

EXAMPLE 2

A granulate with the composition of Example 1 was manufactured. The admixed granulate (130 mg) was filled into capsules.

EXAMPLE 3

Tablets (5 mm) have been manufactured with the following composition:

| | |
|---|---|
| Tibolone | 0.3 mg |
| Basic granulate | 64.175 mg |
| Ascorbylpalmitate | 0.2 mg |
| Magnesium stearate | 0.325 mg |

The composition of the basic granulate (carrier):

| | |
|---|---|
| Potato starch | 10% |
| Lactose | 90% |

The basic granulate has been manufactured in a Fluid Bed Granulator, using a starch mucilage as binding liquid.

Approx. 10% of basic granulate was premixed with Tibolone and ascorbylpalmitate. After screening the premix through a 250 μm sieve, the rest of the basic granulate was added and mixing was continued. Finally, magnesium stearate was admixed and the final mixture was tabletted to tablets with a diameter of 5 mm.

EXAMPLE 4

Capsules have been filled with 130 mg of the admixed final granulate, manufactured in Example 3.

EXAMPLE 5

The tablets of Example 3 were stored for 3 months at 40 degrees Celsius. The content after storage (in %) of Tibolone and the decomposition product Org OM38 are given in the table.

| | Tibolone | Org OM 38 |
|---|---|---|
| 40 degrees/25% rel. humidity | 80 | 13 |
| 40 degrees/75% rel. humidity | 96 | 3 |

As demonstrated, the tablets (65 mg) comprising 10% of starch and 0.3 mg of Org OD14 are most unstable at dry storage conditions.

EXAMPLE 6

Capsules (no. 5) have been filled with 50 mg of admixed granulate (made analogously to Example 1) on a Bosch capsule filling machine (Formulation 1). The stability of this capsule product is compared with tablets, manufactured with the composition as described in Example 3 (Formulation 2). The content of decomposition products Org OM38 and Org OM08 (in %) of both products after storage of 2 months at 30 degrees Celsius/45% rel. humidity are depicted in the table.

| | Formulation 1 | Formulation 2 |
|---|---|---|
| Tibolone (Org OD14) | 0.3 mg | see Example 3. |
| Basic granulate | 49.70 mg | |

The composition of the basic granulate (carrier):

| | |
|---|---|
| Lactose | 58.7% |
| Corn starch | 40.2% |
| Magnesium stearate | 1.0% |
| Ascorbyistearate | 0.1% |

|  | Formulation 1 | Formulation 2 |
|---|---|---|
| Org OM38 | 2.52 | 3.81 |
| Org OM08 | 0.15 | 0.97 |

The data demonstrate that the incorporation of 40% of starch (Formulation 1) improves the stability when compared with preparations only comprising 10% of starch (Formulation 2).

EXAMPLE 7

Basic granulates (carriers) for the capsules have been manufactured comprising various concentrations of corn starch. Admixing of the basic granulate with excipients and Org OD 14 was performed as described in Example 3.

Capsules were filled with admixed granulate with a composition per 65 mg of:

|  | Formulation I | Formulation II | Formulation III |
|---|---|---|---|
| Tibolone (Org OD14) | 0.3 mg | 0.3 mg | 0.3 mg |
| Ascorbylpalmitate | 0.2 mg | 0.2 mg | 0.2 mg |
| Magnesium stearate | 0.325 mg | 0.325 mg | 0.325 mg |
| Basic granulate to | 65 mg | 65 mg | 65 mg |

Composition basic granulate (carrier)

|  |  |  |  |
|---|---|---|---|
| Hydroxypropylcellulose | — | 3% | 3% |
| Potato starch | 10% | 50% | 97% |
| Lactose | 90% | 47% | 0% |

The capsules have been stored for 3 months at 40 degrees Celsius at a dry condition (25% relative humidity). The contents, after storage, of the decomposition products Org OM38 and Org OM 08 (in %) are depicted in the Table.

|  | Formulation I | Formulation II | Formulation III |
|---|---|---|---|
| Org OM38 | 6.14 | 5.13 | 3.17 |
| Org OM08 | 1.22 | 0.24 | 0.16 |

It can be concluded that the stability of Org OD14 is significantly improved with increasing starch concentration, in particular relatively low amounts of decomposition product are found in Formulation III with approximately 97% of starch.

EXAMPLE 8

Tablets have been manufactured according to the procedure as described in Example 3. The composition of the tablets:

|  | Formulation A | Formulation B |
|---|---|---|
| Tibolone (Org OD14) | 0.3 mg | 0.3 mg |
| Ascorbylpalmitate | 0.1 mg | 0.1 mg |

-continued

|  | Formulation A | Formulation B |
|---|---|---|
| Magnesium stearate | 0.325 mg | 0.325 mg |
| Basic granulate to | 65 mg | 65 mg |

Composition basic granulate (carrier):

|  |  |  |
|---|---|---|
| Hydroxypropyl cellulose | 3% | 3% |
| Corn starch | 50% | 97% |
| Lactose | 47% | — |

The tablets have been stored for 3 months at 40 degrees at 25% relative humidity. The contents, after storage, of Tibolone and the decomposition products Org OM38 and Org OM08(in %) are depicted in the Table.

|  | Formulation A | Formulation B |
|---|---|---|
| Org OM38 | 3.75 | 1.85 |
| Org OM08 | 1.52 | 0.39 |

The contents of decomposition products after storage of the formulation with approx. 97% of starch is significantly lower than found in tablets with 50% of corn starch.

EXAMPLE 9

Capsules (no. 4) were manufactured with the following composition (mg):

|  |  |
|---|---|
| Tibolone (Org OD14) | 0.625 |
| Ascorbylpalmitate | 0.1 |
| Magnesium stearate | 0.06 |
| Basic granulate to | 60.0 |

Composition basic granulate (carrier) in mg:

|  |  |
|---|---|
| hydroxypropylcellulose | 1.776 |
| Corn starch | 57.41 |

The basic granulate had been manufactured with the WSG fluid bed granulator according to a standard granulation procedure.

A premix was manufactured by mixing for 10 minutes in the Rhonrad: 54.1 gram of Org OD14, 8.375 gram of ascorbylpalmitate and 365 gram of basic granulate. After sieving the premix was mixed with the rest of the basic granulate and subsequently admixed with magnesium stearate for 5 minutes using the Rhonrad. The active granulate (approx. 5 kg) was filled into capsules no. 4 using the Bosch machine.

EXAMPLE 10

Tablets were manufactured having the following composition (mg):

| | |
|---|---|
| Tibolone (Org OD14) | 0.625 |
| Ascorbylpalmitate | 0.1 |
| Magnesium stearate | 0.06 |
| Basic granulate | to 60 |

Composition basic granulate (carrier) in mg:

| | |
|---|---|
| Corn starch binder | 3.6 |
| Corn starch | 56.4 |

The basic granulate was manufactured with a WSG fluid bed granulator with corn starch mucilage as binder.

The active granulate was manufactured as described in Example 9. The granulate was compressed on a Korsch PH106 to tablets with a diameter of 5 mm.

EXAMPLE 11

Analogously to Examples 1 and 2, basic granulates (11A and 11B) in accordance with the invention were formed and compared with a basic granulate (11C) not according to the invention. Dosage units (capsules and tablets) were stored at 40° C. and 25% relative humidity for 6 months and the residual percentage of tibolone as determined.

| Ingredient | A mg | B mg | C mg |
|---|---|---|---|
| tibolone | 1.0 | 0.5 | 1.0 |
| lactose | 28.4 | 28.7 | 88.4 |
| corn starch | 20.0 | 20.2 | 10.0 |
| magnesium stearate | 0.5 | 0.5 | 0.5 |
| ascorbyl stearate | 0.1 | 0.05 | 0.1 |
| % starch in carrier | 41.3% | 41.3% | 10.2% |
| % tibolone residue | 94.6 | 91.7 | 88.8 |

What is claimed is:

1. A stabilized pharmaceutical dosage unit comprising tibolone, in an amount of from 0.1% to 10% by weight of the dosage unit, and a pharmaceutically acceptable carrier, the carrier comprising a water-insoluble starch product in an amount at least 40% by weight of the dosage unit.

2. A dosage unit according to claim 1, wherein the starch content in the carrier is at least 50% by weight.

3. A dosage unit according to claim 2, wherein the starch content in the carrier is 90–100% by weight.

4. A dosage unit according to claim 1, wherein the starch product is selected from the group consisting of Starch 1500, potato starch, corn starch, wheat starch, and mixtures thereof, the group including modified starches, agglomerated starches, and granulated starches.

5. A stabilized pharmaceutical dosage unit comprising:

tibolone, and a pharmaceutically acceptable carrier, the carrier comprising a water-insoluble starch product in an amount of more than 10% by weight of the dosage unit, wherein the tibolone is present in an amount of 2% by weight or less.

6. A dosage unit according to claim 5, wherein the quotient of the weight percentage of the tibolone medicinal agent in the dosage unit and the weight percentage of the starch product in the carrier is at most 0.02.

7. A dosage unit according to claim 6, wherein said quotient is at most 0.01.

8. A dosage unit according to claim 1, comprising up to 5% by weight of a stabilizer selected from the group consisting of antioxidants, chelating agents, and mixtures thereof.

9. A dosage unit according to claim 8, wherein the stabilizer is selected from the group consisting of ascorbyl palmitate, ascorbyl stearate, sodium ascorbate, and mixtures thereof.

10. A method of making a dosage unit according to claim 1, the method comprising the steps of providing a carrier of the desired composition, mixing tibolone with a portion of the eventually needed amount of carrier to obtain a pre-mix, screening the pre-mix, further mixing it with the remaining portion of the carrier, and finally admixing with lubricant.

11. A method of increasing the stability of tibolone containing pharmaceutical dosage units, comprising:

mixing from 0.01 to 10% of tibolone with a pharmaceutically acceptable carrier comprising starch in an amount greater than 40% by weight of the carrier.

* * * * *

UNITED STATES PATENT AND TRADEMARK OFFICE
CERTIFICATE OF CORRECTION

PATENT NO. : 6,399,594 B2
DATED : June 4, 2002
INVENTOR(S) : De Haan et al.

It is certified that error appears in the above-identified patent and that said Letters Patent is hereby corrected as shown below:

<u>Column 10,</u>
Line 39, claim 11 should read:
11. A method of increasing the stability of tibolone containing pharmaceutical dosage units, comprising:
    mixing from 0.1 to 10% of tibolone with a pharmaceutically acceptable carrier comprising starch in an amount greater that 40% by weight of the dosage unit.

Signed and Sealed this

Twenty-fourth Day of February, 2004

JON W. DUDAS
*Acting Director of the United States Patent and Trademark Office*